(12) United States Patent
Hoeche (10) Patent No.: US 8,071,960 B2
(45) Date of Patent: Dec. 6, 2011

(54) METHOD AND APPARATUS FOR PRODUCING SAMPLES FOR TRANSMISSION ELECTRON MICROSCOPY

(75) Inventor: Thomas Hoeche, Halle (DE)

(73) Assignee: 3D-Micromac AG (DE)

( * ) Notice: Subject to any disclaimer, the term of this patent is extended or adjusted under 35 U.S.C. 154(b) by 294 days.

(21) Appl. No.: 12/576,777

(22) Filed: Oct. 9, 2009

(65) Prior Publication Data

US 2010/0090108 A1    Apr. 15, 2010

(30) Foreign Application Priority Data

Oct. 10, 2008 (DE) .......................... 10 2008 052 006

(51) Int. Cl.
*H01J 37/20* (2006.01)
*H01J 37/244* (2006.01)

(52) U.S. Cl. .................. 250/440.11; 250/251; 250/306; 250/311; 250/441.11

(58) Field of Classification Search .................. 250/251, 250/306, 311, 440.11, 441.11, 442.1
See application file for complete search history.

(56) References Cited

U.S. PATENT DOCUMENTS

| | | | | |
|---|---|---|---|---|
| 5,453,617 A * | 9/1995 | Tsuneta et al. | ................. | 250/311 |
| 5,500,535 A * | 3/1996 | Jing | .......................... | 250/440.11 |
| 5,609,284 A | 3/1997 | Kondratenko | | |
| 5,611,946 A | 3/1997 | Leong et al. | | |
| 5,650,621 A * | 7/1997 | Tsuneta et al. | ................. | 250/311 |
| 6,538,254 B1 * | 3/2003 | Tomimatsu et al. | ..... | 250/442.11 |
| 6,717,156 B2 * | 4/2004 | Sugaya et al. | ........... | 250/440.11 |
| 6,720,522 B2 | 4/2004 | Ikegami et al. | | |
| 6,828,566 B2 * | 12/2004 | Tomimatsu et al. | ..... | 250/442.11 |
| 6,858,851 B2 * | 2/2005 | Tomimatsu et al. | ..... | 250/442.11 |
| 6,927,400 B2 * | 8/2005 | Rasmussen | .............. | 250/442.11 |
| 6,982,429 B2 | 1/2006 | Robinson et al. | | |
| 7,071,475 B2 * | 7/2006 | Tomimatsu et al. | ..... | 250/442.11 |
| 7,138,628 B2 * | 11/2006 | Tomimatsu et al. | .......... | 250/306 |
| 7,227,140 B2 * | 6/2007 | Skidmore et al. | ............. | 250/307 |
| 7,397,050 B2 * | 7/2008 | Tomimatsu et al. | ..... | 250/492.21 |
| 7,397,052 B2 * | 7/2008 | Tomimatsu et al. | ..... | 250/492.21 |

(Continued)

FOREIGN PATENT DOCUMENTS

DE    102004001173 A1    8/2005
(Continued)

OTHER PUBLICATIONS

McCaffrey, "Improved TEM Samples of Semiconductors Prepared by a Small-Angle Cleavage Technique", Microscopy Research and Technique (1993), vol. 24, pp. 180-184.

(Continued)

*Primary Examiner* — David A Vanore
(74) *Attorney, Agent, or Firm* — Akerman Senterfitt (57) ABSTRACT

In the case of a method for producing samples for transmission electron microscopy, a sample is prepared from a substrate of a sample material. To this end, the sample material is irradiated by means of a laser beam along an irradiation trajectory in order to produce a weak path in the sample material. The irradiation is controlled such that the weak path crosses a further weak path, which is likewise preferably produced by laser irradiation, running in the sample material, at an acute angle in a crossing region. The substrate is broken along the weak paths. A sample is thereby produced which has a wedge-shaped sample section bounded by fracture surfaces and has in the region of a wedge tip at least one electron-transparent region.

36 Claims, 6 Drawing Sheets

U.S. PATENT DOCUMENTS

| | | | |
|---|---|---|---|
| 7,408,178 B2* | 8/2008 | Tappel | 250/492.21 |
| 7,414,252 B2* | 8/2008 | Moore et al. | 250/492.21 |
| 7,504,623 B2* | 3/2009 | Fischione et al. | 250/309 |
| 7,511,282 B2* | 3/2009 | Agorio et al. | 250/442.11 |
| 7,525,108 B2* | 4/2009 | Tomimatsu et al. | 250/492.21 |
| 7,544,953 B2* | 6/2009 | Goodman | 250/440.11 |
| 2003/0147135 A1 | 8/2003 | Ozygus | |
| 2003/0183776 A1* | 10/2003 | Tomimatsu et al. | 250/442.11 |
| 2005/0178980 A1* | 8/2005 | Skidmore et al. | 250/492.21 |
| 2005/0184234 A1* | 8/2005 | Nakayama | 250/311 |
| 2006/0022148 A1* | 2/2006 | Fischione et al. | 250/492.21 |
| 2006/0219676 A1 | 10/2006 | Taylor et al. | |
| 2007/0170162 A1 | 7/2007 | Haupt et al. | |
| 2008/0068707 A1* | 3/2008 | Goodman | 359/368 |
| 2008/0073535 A1* | 3/2008 | Hong et al. | 250/311 |
| 2008/0090382 A1 | 4/2008 | Fujii et al. | |
| 2008/0296498 A1* | 12/2008 | Hong | 250/311 |

FOREIGN PATENT DOCUMENTS

| | | |
|---|---|---|
| JP | 2007129143 A | 5/2007 |

OTHER PUBLICATIONS

McCaffrey, "Small-Angle Cleavage of Semiconductors for Transmission Electron Microscopy", Ultramicroscopy (1991), vol. 38, pp. 149-157.

* cited by examiner

METHOD AND APPARATUS FOR PRODUCING SAMPLES FOR TRANSMISSION ELECTRON MICROSCOPY

The following disclosure is based on German Patent Application No. 10 2008 052 006.3 filed on Oct. 10, 2008, which is incorporated into this application by reference.

BACKGROUND OF THE INVENTION

1. Field of the Invention

The invention relates to a method for producing samples for transmission electron microscopy, and to an apparatus suitable for carrying out the method.

2. Description of the Related Prior Art

Since their introduction in the 1930s, transmission electron microscopes have found wide application in various branches of science and industry. Because of the resolution which is substantially better by comparison with light microscopy and lies in the sub-angstrom range for the currently best appliances, the microstructure and nanostructure of various types of preparations can be examined in great detail.

Particularly in the field of characterization of solids, information can be obtained on the atomic scale with the aid of transmission electron microscopy (TEM). In this case, it is possible on the one hand to examine the arrangement of the atoms, while on the other hand it is also possible to access the chemical composition and the electronic structure with the aid of dedicated analysis methods such as x-ray spectroscopy and electron energy loss spectroscopy. The presence of fewer, in exceptional cases even individual, atoms can be demonstrated in the case of electron energy loss spectroscopy.

Up to a few years ago, the electron optical systems used in transmission electron microscopes were not sufficiently good to allow images and analyses at the theoretical spatial resolution limit. The introduction of highly complex aberration correctors and monochromators, which enable control via limiting parameters such as the aperture aberrations and chromatic aberrations of electron lenses, a very much closer approach with regard to spatial resolution limit is presently being made. Whereas it was possible in the 1990s to attain spatial resolutions in the sub-angstrom range only by means of very high acceleration voltages of 1 MeV and more, and to attain the very short electron wavelengths associated therewith, it is presently possible through the use of corrector lenses to advance into the sub-angstrom resolution range even with moderate acceleration voltages of, for example, 80 to 300 keV. This results in advantages with respect, inter alia, to the frequently problematic beam damage of the very thin preparations, which should have only a very slight thickness (order of magnitude of a few 10 nm) for highly resolved imaging and analysis in the examined range.

Consequently, the question of efficient and low-damage methods for preparing the samples for transmission electron microscopy, which are also referred to below for short as TEM samples, arises to an increasing extent. The invention relates in this case specifically to a method for producing TEM samples in which is prepared from a substrate of a sample material a sample which has a wedge-shaped sample section which is bounded by wedge surfaces and has in the region of the wedge tip at least one electron-transparent region.

It is true that thinning is possible in principle in a purely mechanical way, but it requires great manual skill in order to lead to reproducible sample quality at least to some extent. Moreover, there is presently a multiplicity of partially very complex technologies for producing adequately thin, electron-transparent areas on TEM samples. These include, in particular, mechanical prethinning (grinding, polishing, cavity grinding), which is followed by an ion beam etching process, the cutting out of thin sections with the aid of a focused ion beam, and ultramicrotomy.

DE 10 2004 001 173 B4 describes a method for preparing TEM samples in the case of which material is removed from a substrate of a sample material by means of ultrashort pulse laser ablation in a vacuum chamber, this being done in such a way that there remains a narrow web which is subsequently bombarded in a flat angle with an inert gas ions such that an electron-transparent area is produced in the region of the web. Numerous further conventional preparation methods for TEM samples are described in the introduction to the description in this publication.

The methods used for ion beam thinning go hand in hand in principle with the formation of a near-surface amorphization/damage of the sample material, the extent of which is a function of the acceleration voltage of the ions. The amorphization/damage can be more than 10 nm, for example, when use is made of 3 keV gallium ions, while damage thickness of between 3 and 6 nm is frequently observed in the case of typical low-angle ion etching at 3 keV. According to results of relevant investigations, a reduction to below 1 nm is scarcely possible even when use is made of low-energy ion beams (typically 200 eV to 500 eV energy).

For the special case of substrates made from materials with defined cleavage planes, the so-called "Small Angle Cleavage Technique (SACT)" has been proposed (see, for example, J. P. McCaffrey, Ultramicroscopy 38, 149 (1991) or J. P. McCaffrey, Microscopy Research and Technique 24, 180 (1993)). In the case of a piece of a sample material thinned by grinding, with this technique a diamond tip introduces parallel scratch paths of approximately 500 µm width in the direction which assumes an angle of approximately 18.5° relative to a known cleavage plane of the sample material. Subsequently, the preparation is broken along the scratch paths and along the material-specific cleavage plane. In favourable cases, the breaking of the samples results in a tapering preparation with an enclosed angle of approximately 18.5° between the fracture surfaces. In the ideal case, electron-transparent areas which can be examined by means of TEM are located at the outermost end of the wedge-shaped sample section. An advantage of this technique consists in that because of the missing action of ion beams, the prepared TEM samples have no amorphization caused by preparation, and are free from chemical contaminations. Ideally, atomically flat surfaces result on the wedge-shaped sample section. However, the possibilities for using the method are restricted, because it can be used in essence only with sample materials with crystallographically defined cleavage planes. In addition, the method does not lead as a rule to reproducible results. Furthermore, it is difficult to impossible for it to be automated. Finally, it is scarcely possible to implement even a target preparation, since the exact location of the crack initiation cannot be determined accurately enough owing to the coarse scoring.

It is particularly difficult and complicated to prepare cross-sectional preparations that are intended to enable examination of layers, layer systems or structured surfaces substantially perpendicular to the surface normals of the layer structures. Such questions arise to a particular degree in the semiconductor industry, where many thousand cross-sectional preparations are inspected per year in transmission electron microscopes for the purpose of quality control and fault analysis. The benefit of transmission electron microscopy resides here, inter alia, in an extremely high spatial resolution which enables the examination of ever smaller structures on structured semiconductor components. It is becoming increasingly evident that the preparation of high-quality TEM samples with sufficiently thin electron-transparent areas is the step which is limiting throughput. This circumstance is frequently countered by procuring a number of preparation machines, but this, by way of example, is associated with high costs in the case of systems for focused ion beam (FIB) processing.

A plurality of boundary conditions which are to be rendered compatible only with difficulty are typically to be considered when examining structured semiconductor components in the course of quality control and fault analysis. What is frequently involved is to obtain cross-sectional preparations from structured sample material in the case of which the electron-transparent area suitable for examination lies at a position which can be determined with great accuracy and can ideally be derived from the positioning in machines from the process chain. This task is denoted in specialist circles as "target preparation" (or "site-specific preparation"). This target preparation should be performed as quickly as possible so that the results of the quality control can be fed back quickly into the production process of the components. Furthermore, the sample preparation technology should be optimized so as largely to avoid introducing artefacts into the preparation. Typical artefacts include near-surface amorphization (problematic, for example, when cutting out with the aid of a focused ion beam) as well as structural modifications, diffusion, phase changes owing to heat input etc. Finally, the attempt is made, particularly in industrial use, to automate the preparation process as far as possible in order to be able to attain reproducible preparation results in as wide a process window as possible.

SUMMARY OF THE INVENTION

It is one object of the invention to provide a method for producing samples for transmission electron microscopy which enables TEM samples to be produced quickly in a way that can be localized effectively and reproduced and causes little damage in conjunction with a multiplicity of different sample materials.

It is another object of the invention to enable cross-sectional preparations made from materials provided with layer structures, for example structured semiconductor materials, to be obtained in an accurate and reproducible fashion with little damage.

It is yet another object of the invention to employ inventively prepared TEM samples so as to carry out imaging and analysis with high spatial resolution with the use of aberration-corrected medium voltage transmission electron microscopes.

It is a further object of the invention to provide a preparation apparatus which is suitable for carrying out the method and with the aid of which it is possible for TEM samples which are prepared semiautomatically or fully automatically with little damage and have electron-transparent areas which can be localized definitely to be reproduced in a short time.

As a solution to these and other objects, the invention, according to one formulation, provides a method for producing samples for transmission electron microscopy, comprising: preparing from a substrate of a sample material a sample which has a wedge-shaped sample section which is bounded by wedge surfaces and has in the region of a wedge tip at least one electron-transparent region, the preparing step comprising: irradiating the sample material by means of a laser beam along a first irradiation trajectory in order to produce a first weak path in the sample material, the irradiation being controlled such that the first weak path crosses a second weak path, running in the sample material, at an acute angle in a crossing region; and breaking the substrate along the first weak path and along the second weak path.

Advantageous developments are specified in the dependent claims. The wording of all the claims is incorporated into the description by reference.

The method can produce samples for transmission electron microscopy (TEM samples) by virtue of the fact that there is prepared from a substrate of a sample material a sample which has a wedge-shaped sample section which is bounded by wedge surfaces and has in the region of the wedge tip at least one electron-transparent region. To this end, the sample material is irradiated by means of a laser beam along a first irradiation trajectory in order to produce a first weak path in the sample material. The irradiation is controlled in this case such that the first weak path crosses a second weak path, running in the sample material, at an acute angle in a crossing region. Subsequently, the substrate is broken along the first weak path.

The breaking along the second weak path is likewise performed as a rule after the production of the first weak path. The breaking operations can be introduced simultaneously or in a fashion offset in time. However, it is also possible to break the substrate along the second weak path as early as before the production of the first weak path. In this case, the first weak path leads as far as into the vicinity, or directly as far as an already existing fracture surface of the substrate.

The "crossing region of weak paths" is in this case that area in which there is a meeting of weak paths converging at an acute angle or lines of preferred crack propagation defined by the weak paths.

The weak paths are spatially defined, substantially linear weak regions of the material. The weak paths constitute preferred locations of crack initiation or crack propagation in the event of mechanical loading of the sample material, and ensure the production in the target area of fracture surfaces which taper towards one another at an acute angle and form the wedge surfaces of the wedge-shaped sample section. The wedge-shaped sample section can therefore be bounded by atomically smooth surfaces. There is no need for subsequent processing steps such as, for example, ion beam etching, and so it is even possible for no amorphization, caused by preparation, of the wedge surfaces of the sample section to occur. An advantage over other methods, such as focused ion beam (FIB) processing or ion beam etching is thus to be seen in an extreme shortening of the preparation time, which can lie in the range of a few seconds when no account is taken of the mounting on a carrier. A second substantial advantage is the avoidance of near-surface amorphization which occurs in the case of conventional methods owing to the contact that is made with an ion beam. It is certainly true that the thickness of the amorphization can sometimes be reduced by reducing the ion acceleration voltage, but the amorphization cannot be prevented entirely in principle when use is made of ion beam thinning. Moreover, a target preparation is also possible on the micrometer scale, since the irradiation with the aid of the laser beam can be controlled spatially such that the crossing region of the weak paths falls precisely into the desired inspection area (target area) inside the sample material.

By way of example, instead of mechanical scoring it is possible for laser-based production of a weak path, and the defined localization, associated therewith, of a track of preferred crack initiation or crack propagation to be carried out on samples which have a defined cleavage plane which can be used as a natural second weak path, prescribed by the crystalline structure of the sample material, inside the sample material. However, it is preferred for the sample material to be irradiated along a second irradiation trajectory by means of a laser beam in order to produce the second weak path such that the two weak paths running at an acute angle to one another are produced artificially by laser processing. Consequently, the sample preparation method is rendered substantially independent of the sample material, and so it is even possible to prepare materials without defined cleavage planes, for example materials of glass-like structure. In addition, both the position of the crossing region between weak paths and the orientation of the wedge produced inside the sample material can be precisely determined independently of the structure of the sample material such that every degree of freedom exists with regard to position and orientation of the inspection area of interest.

Depending on sample material and the intended inspection method, the first and the second weak paths are preferably orientated relative to one another such that the crossing angle present between them in the crossing region and which defines the later wedge angle of the sample is 25° or less. In many cases, crossing angles of less than 20° are advantageous, particularly in the range from 15° or less. Depending on sample material, the wedge angles can also be relatively small, for example as far as down to 5° to 10°. In these cases, electron-transparent areas of sufficient lateral size and a sufficiently small thickness are produced with particular frequency.

The sample material can be monocrystalline, partially crystalline, polycrystalline or else amorphous. Materials which are substantially accessible to sample preparation are all adequately brittle materials, in particular inorganic non-metallic materials, as well as such materials that lack crystallographically defined cleavage planes (for example glasses).

In the case of applications in the semiconductor industry, for example for the quality control of semiconductor wafers which are structured on a wafer surface by means of microlithography or in some other way, the sample material frequently substantially consists of a semiconductor material such as silicon, germanium etc., and/or of one or more compounds based on one or more semiconductor materials. Heterostructures having layer materials of different doping and/or function layers of another composition can be located on one surface of the sample material.

The starting point for sample preparation is generally a block of the sample material of suitable size which forms the substrate or from which the substrate is fabricated by material-removing processing. The substrate is normally a substantially plane-parallel thin section which can consist of a monocrystalline, partially crystalline, polycrystalline or else amorphous sample material, or of a combination of a plurality of materials. The substrate is selected such that the inspection area or target area, whose structure is later to be examined by means of TEM, lies near the front side of the substrate. The irradiation by means of laser radiation is preferably performed from the rear side, opposite the front side, of the substrate, particularly in such a way that the inspection area lying near the front side lies outside the weak path. It is possible to achieve as a result of this rear irradiation that the area of the sample material which is to be inspected is not itself damaged by the laser radiation such that its structure is present for TEM inspection substantially without modification by laser irradiation. A close spatial delimitation of the material weakening or material damage can be promoted by suitable beam guidance with a large beam expansion, subsequent focusing with a large convergence angle (or high numerical aperture) and, in association therewith, a low depth of focus, for example by setting the Rayleigh length such that the damage threshold fluence, that is to say that power density above which instances of damage can occur, is not exceeded on the front side.

For most applications, it has proved to be advantageous when before the irradiation the substrate has a substrate thickness between approximately 30 µm and approximately 500 to 550 µm in the area provided for the laser processing. It is thereby possible in most cases to ensure a crack propagation into the examination area of interest. If the initial material is too thick for this, it can be brought to the advantageous substrate thickness by grinding and/or another type of material-removing processing.

Depending on the sample material and on the desired preparation, numerous variants are possible with regard to the laser processing, that is to say the modifying and/or ablating or damaging irradiation of the sample material by laser radiation.

In the case of one method variant, the irradiation is carried out by means of laser radiation to which the sample material is partially transparent. Under these conditions, the irradiation can be controlled such that an inner weak path lying in the interior of the substrate at a spacing from the substrate surface is produced. In the case of this internal processing, largely undamaged areas which can be examined by means of TEM can be present in the direction of the substrate normals to both sides of the weak path in the finished preparation. However, it is sufficient as a rule when undamaged areas exist on the side averted from the incoming beam side.

Particularly for those cases where operations proceed with partially transparent sample material and/or with a damage zone lying inside the sample, and/or a weak zone, the substrate can be polished on its rear side before being irradiated in order to reduce the surface roughness and/or to produce a relatively smooth radiation entrance surface, it thereby being possible to improve the focusability of the laser beam spot onto a defined area in the interior of the sample. Experiments have shown that excessively rough surfaces can strongly scatter the laser radiation to be coupled such that the position of the weak path can be localized with less precision and the weakening action can be reproduced to a lesser extent than in the case of a polished beam entrance surface. It is preferred to produce by the polishing a radiation entrance surface with an optical quality which can, for example, have a mean depth of roughness $R_a$ of less than 10 nm.

In the case other variants, which are also denoted below as "laser scoring", the irradiation is controlled so as to produce a weak path near the surface on the irradiation side of the substrate. The method variant of the laser scoring utilizes the rear-side, superficial scoring, particularly with the aid of a laser, whose radiation is strongly absorbed in the sample material. However, the laser scoring can also be carried out on materials which are partially transparent or transparent to the laser radiation, and can therefore be used universally in a fashion largely independent of the substrate material. For this method variant, it is not necessary as a rule to polish the irradiation surface before the irradiation, and this simplifies and accelerates the entire process of sample production. However, it can be entirely sensible for the irradiation surface to be polished.

In order when starting from a weak path to ensure a geometrically defined fracture in the sample material, it has proved to be advantageous when the laser radiation produces a depth of damage which corresponds at least to two thirds of the thickness of the substrate in the region of the weak path. It is frequently more advantageous when the depth of damage reaches even further, for example as far as ⅘ of the sample thickness. In the case of both methods, an important criterion for the design of the depth of damage is the intactness of the structure to be inspected on the substrate front side, which should be modified as little as possible structurally and chemically. Samples which have a layer structure in the inspection area are particularly sensitive in this regard.

Although it is possible for the power density acting on the substrate to remain substantially constant during traversal of an irradiation trajectory, in the case of many method variants a spatially dependent control is carried out in order to vary the power density acting on the substrate during traversal of an irradiation trajectory. This can be performed automatically with the aid of an appropriately configured and/or programmed control device, and be very advantageous for various reasons.

Particularly in the case of very sensitive sample materials, it can be advantageous when the irradiation is controlled such that an undamaged area remains in the immediate vicinity of the crossing region. In this case, the weak paths produced by irradiation do not reach up to the theoretical crossing of the weak lines defined by the weak paths, but end in the vicinity of the imaginary crossing point at a specific spacing from the theoretical crossing point. The guidance of the method can also be described in the fact that the first weak path runs in a target area at an acute angle to a second weak path running in the sample material, or that the first weak path approaches a second weak path running in the sample material in the region of a crossing of weak paths at an acute angle without a crossing actually taking place. The spacing from the theoretical crossing point is preferably to be set such that a crack propagation inside the sample material can continue along a weak path through the crossing region, slightly damaged or not damaged, to the opposite beginning of the same weak path, such that the undamaged area is, so to say, bridged by the propagating crack. The spacing, or the radius of the largely undamaged area can be, for example, less than 300 µm, it can be, for example, between approximately 50 µm and approximately 250 µm, in particular in the range between approximately 100 µm approximately 200. The radius should be at least 0.5 µm or at least 1 µm, in order to ensure an undamaged electron-transparent area of sufficient size in the region of the wedge tip.

The local interruption or reduction in the damaging irradiation during traversal of an irradiation trajectory can be attained in different ways. In the case of one variant, the laser beam is briefly interrupted at a suitable point by means of a controllable shutter or another beam interrupting device. This is possible for all types of laser, in particular also in the case of continuous wave (cw) lasers. In the case of other variants, the local interruption is achieved by briefly turning off the laser during traversal of an irradiation trajectory or suppressing the pulse initiation when the crossing region is passed over. This is perfectly possible in the case of pulsed lasers, for example. It is also possible to achieve local interruption of or reduction in the damaging irradiation during traversal of an irradiation trajectory by means of a local power control of the effective output power of the laser, either at the laser itself or with the aid of a controllable attenuator positioned in the beam path. In the case of all variants, it is possible to achieve in the region of the wedge tip sections of wedge surfaces which are completely free of damage caused by laser irradiation. Moreover, this prevents or (by comparison with continuous weak paths) reduces, a potentially undesired accumulation of heat in the region of the wedge tip.

A local control for varying the power density acting on the substrate during traversal of an irradiation trajectory can also be used to entirely sever the substrate far from the crossing region of the irradiation trajectories at the start and/or at the end of an irradiation trajectory, thus producing notches which facilitate a later localized initiation of breakage.

Particular advantages are offered by the method when the sample material has in the inspection area a layer structure with one or more layers and one or more interfaces. Here, the weak paths can be positioned so as to produce wedge surfaces which are substantially perpendicular to at least one of the interfaces, it thereby being possible to carry out a transmission electron microscopic examination substantially perpendicular to the surface normal of the interface.

Two parameters, specifically the wavelength and the temporal control of the irradiation, in particular the pulse duration, are chiefly important in setting suitable laser parameters for the irradiation. Whereas the wavelength is to be selected as far as possible with regard to the sample material such that either a partial transparency of the sample material (for the internal processing) or as complete an absorption as possible of the laser radiation in the sample material occurs (for the laser scoring), the pulse duration influences the mechanism of interaction between the laser radiation and sample material, and thus the extent of the heat-affected zone. Whereas ultrashort pulse lasers can couple into the electronic structure of the sample material with typical pulse durations in the range of picoseconds (ps) or femtoseconds (fs) and can thus lead to a quasi-athermal ablation, interaction with short pulse lasers whose pulses typically have pulse lengths in the range of nanoseconds (ns) or microseconds (µs) or the emitting interaction with continuously emitting lasers (continuous wave laser, cw laser) frequently leads to a local fusing of the sample material with subsequent vaporization of the fused material. As a rule, short pulse lasers and cw lasers heat up the sample to be processed much more strongly than the ultrashort pulse lasers.

All known types of laser are suitable in principle for the sample preparation technology proposed here. Thus, for example, short pulse lasers or cw lasers can be used to irradiate ceramic materials having a poor thermal conductivity, which will not essentially suffer microstructural modification owing to reverse heating. For numerous applications, for example in the case of the preparation of dielectrics or semiconductor materials, the irradiation is, however, preferably carried out by means of an ultrashort pulse laser, since these can also be used, by means of multiphoton absorption, to process materials which are actually transparent to the wavelength used. The latter phenomenon is coupled to high power densities at which nonlinear optical effects can cause the energy of the two or more photons in an excitation process to be able to add together, and thus, for example, able to overcome in dielectric materials bandgaps which lie far beyond the energy of an individual photon.

In order to be able to use a single laser source to set irradiation parameters which are optimum for a multiplicity of different sample materials, it is provided in a preferred variant to use a tunable laser source to produce the laser radiation in order to be able to set the respectively optimum wavelengths for different sample materials. As regards the selection of a suitable wavelength, it is possible, for example, to use optical parametric amplifiers (OPAs). The latter can be used together with a fundamental laser wavelength and a white light source to produce a tunable spectrum of laser wavelengths which are greater than the fundamental wavelength. For example, commercial laser systems (Clark-MXR, inc.) are available; by means of optical parametric amplification, they can output any wavelength from a wavelength range from approximately 1.5 µm to approximately 2.5 µm on the basis of a seed laser in the wavelength of 775 nm. Others reach a tunable range from 189 nm to 20 µm.

At present, wavelengths of between approximately 248 nm (KrF excimer laser) and a maximum of 3 µm appear to be useful for many applications. At shorter wavelengths, the outlay on beam guidance rises because the beam path should be purged with protective gas or evacuated in order to avoid absorption. At wavelengths above approximately 3 µm, there is a rise in outlay which must be made to focus the laser beam. The operating wavelength is therefore preferably between approximately 247 nm and approximately 3 µm. Particularly in the range between approximately 1 µm and approximately 2 µm, it is possible, for example, to use fibre lasers which can provide adequate output power together with high beam quality.

In order to exclude feedback of laser radiation into the laser source, it is provided with some variants that the laser radiation is irradiated into the substrate at an inclination to the surface normal of the radiation entrance surface. As a rule, small setting angles of, for example, 5° or less between the beam incidence direction and surface normal suffice to avoid feedback. It is then possible to dispense with expensive optical isolators and other aids. This can be achieved in a simple way by causing a tilting device to incline the holding surface of a substrate holder slightly, or permanently, as required.

The targeted breaking of the substrate along the weak paths can be carried out in different ways. In the case of one method variant, in order to break the substrate, a stretchable film is initially, in particular before introduction of the weak paths, bonded onto a side of the substrate, in particular onto the front side, averted from the beam entrance side, and a force sufficient for crack initiation and/or crack propagation after the introduction of the damage paths is exerted on the substrate by stretching the film, such that said substrate breaks along fracture surfaces defined by the damage structures, thus producing the TEM sample. The film preferably has a region lacking an adhesive layer, for example a, preferably round, cutout, and is bonded onto the damaged substrate in such a way that the region lacking an adhesive layer lies in the region of the crossing of the weak paths. It can thereby be achieved that the extremely sensitive, acute-angled, wedge-shaped ends of the triangles enclosed by the laser trajectories run free and can be used for TEM examination. When use is made of an adhesive film, the fragments remain fixed as a rule after the separation, and this facilitates the further processing.

Alternatively, it is also possible to apply other methods for crack initiation such as, for example, breaking over an edge etc.

The invention also relates to an apparatus for producing samples for transmission electron microscopy which is specifically designed and configured to carry out the method, and which enables the method to be carried out semiautomatically or fully automatically after appropriate setting up by an operator. The apparatus has a substrate holder for holding a substrate made from a sample material; a laser system having a laser radiation source and a beam guiding system for guiding a laser beam onto a beam entrance surface of the substrate; and a movement system for producing a relative movement between the substrate and the laser beam in such a way that the laser beam irradiates the substrate at least along a first irradiation trajectory. Also provided is a control device which can be configured or is configured to carry out the method. The control device can be used to drive the substrate holder, the laser system and the movement system in a way tuned to one another in order to carry out different method variants. The entire device is preferably computer-controlled, the control device including an operating program which allows various method variants to be programmed by inputting a few input parameters, and thereafter causes them to run automatically on the basis of control signals of the control device. The following input parameters, in particular, can belong to the input parameters:

(i) A target area parameter which represents the position or the location of the target area in which a first irradiation trajectory crosses a second weak path at an acute crossing angle. The target area can, for example, be input on the basis of a camera image, or via coordinates relative to a coordinate system which is prescribed by marks fixed in relation to the substrate, (ii) A crossing angle parameter which represents directly or indirectly (for example via a prescribable course of the irradiation trajectories) the crossing angle of the first weak path with the second weak path.

(iii) A profile parameter which represents the profile of at least one irradiation trajectory which can, for example, be rectilinear, kinked or curved.

(iv) A focusing parameter which defines the position of the focal region on the substrate or in the substrate, in order, for example, to select between a surface laser scoring and internal damage. If appropriate, it is also possible to prescribe a spatial arrangement of a plurality of paths relating to the same internal damage path.

(v) One or more laser parameters which define specific beam characteristics of the laser beam focused onto the substrate, for example convergence angle or numerical aperture in the focal region, if appropriate wavelength (in the case of tunable laser sources), if appropriate temporal control of the irradiation, in particular the pulse repetition rate.

(vi) It is optionally possible to input power variation parameters for the position-synchronous, variable control of the laser power acting on the substrate, in order, in particular, to permit such method variants in the case of which the power density of the incident laser beam in the immediate vicinity of the crossing region can be so far reduced over a certain time interval or over a certain distance passed over that an undamaged area remains in the vicinity of the crossing regions. To this end it can also be possible to program the speed of traversal along the trajectories in an appropriately variable fashion.

(vii) Number of passed over occasions, if appropriate with varying parameters (i) to (vi).

Repetition rate and pulse energy can also be set in the case of pulsed laser.

The production of the first weak path and the production of the second weak path can thereafter be carried out automatically, that is to say without the intervention of an operator, with the aid of an appropriately programmable laser processing apparatus.

To the extent that conventional laser microprocessing devices are fundamentally suitable for carrying out the method on the basis of their design with regard to laser source, focusability and controllability of the relative movement between laser beam and substrate holder, said devices can also be used to carry out the method in that at least one of the weak paths, preferably two weak paths running at an acute angle to one another, are thereby produced. The invention therefore also relates to the use of a laser microprocessing system of suitable configurations for carrying out the method.

In addition to stemming from the claims, the above features and further ones also emerge from the description and the drawings, it being possible for the individual features to be respectively implemented on their own or separately in the form of subcombinations for embodiments of the invention and in other fields, and for them to represent advantageous designs capable of protection for themselves.

DETAILED DESCRIPTION OF THE PREFERRED EMBODIMENTS

Figure 1:
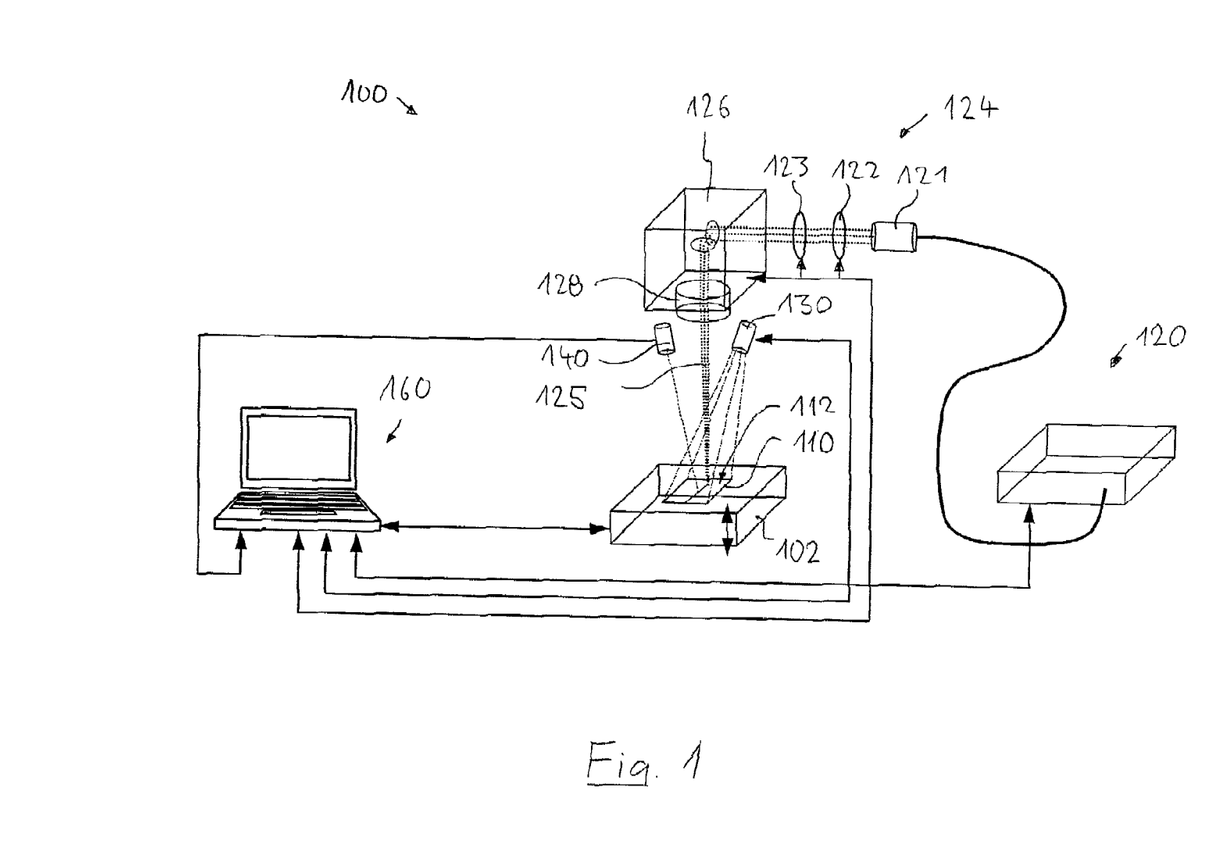
FIG. 1 shows a schematic illustration of essential components of a preparation apparatus for producing samples for transmission electron microscopy by means of laser microprocessing.

FIG. 1 shows a diagrammatic illustration of essential components of an apparatus 100 for producing samples for transmission electron microscopy with the aid of focused laser radiation. The apparatus, which is also referred to as a sample preparation apparatus 100 below, is a laser microprocessing station which is designed as a table appliance and whose components are specifically designed for the purpose and coordinated with one another in order semiautomatically or fully automatically to produce from preprocessed or not specifically preprocessed substrates of different sample materials TEM samples which are suitable for ultrahigh resolution TEM examinations, in particular for TEM examinations with the aid of modern, aberration-corrected transmission electron microscopes largely with the avoidance of preparation artefacts (for example, near-surface amorphization).

A lifting table 102 which can be driven by an electric motor and functions as substrate holder for holding at least one substrate 110 on its top side serving as substrate holding surface is mounted on a machine bed supported so as to damp vibrations and which is, for example, a granite plate (not shown). The lifting table can be assigned a tilting arrangement which enables the lifting table to be tilted if required by a few degrees (for example at most 5°) from the zero position shown in FIG. 1. In the zero position, the top side of the lifting table is aligned horizontally, and therefore perpendicular to the vertical Z-axis or to the mean direction of incidence of the laser beam. It is also possible to provide a permanent inclination of the substrate holding surface with reference to the direction of incidence of the laser beam.

Furthermore, the apparatus 100 has a laser system with a laser radiation source 120 and, fitted thereto, a beam guiding system 124 for guiding the laser radiation and for producing a focused laser beam 125, and can be aligned with an upwardly directed beam entrance surface 112 of the substrate. Use is made in the embodiment of a largely maintenance-free and cost-effective fibre laser 120 which, as an ultrashort pulse laser, is capable of emitting laser pulses with typical pulse lengths in the range of picoseconds (ps, in the range of femtoseconds (fs) for other embodiments).

Depending on the sample material and the desired conduct of the method, the following types of laser are suitable, for example: an erbium or ytterbium fibre laser from MPB Communications Inc. with passive mode coupling (MLFL-P Series with an operating wavelength of $\lambda$=1530 nm-1565 nm (Er) or 1020 nm-1100 nm (Yb), mean output power of up to approximately 200 mW and repetition rate of between 30 MHz and 100 MHz, or a tangerine fibre laser (from Amplitude Systems) with an operating wavelength of $\lambda$=1030 nm, 14-20 W output power and pulse lengths of between less than 100 fs and less than 10 ps as well as repetition rates of between approximately 2 MHz and approximately 30 MHz.

The laser beam expanded with the aid of a beam expander 121 passes through a shutter 122, which can be operated under computer control, and an attenuator 123, which can likewise be set under computer control, and is subsequently deflected by the mirror arrangement of a galvanometer scanner 126 in the direction of a focus optics 128 which focuses a laser beam onto the area of the rear side 112, serving as beam entrance surface, of the substrate. As a telecentric f-theta optics, the focusing optics 128 is adapted to the deflecting range of the galvanometer scanner and the characteristics of the incident laser beam in such a way that the focused laser beam essentially has the same beam characteristics inside a two-dimensionally extended working area on the flat substrate surface at each focusing position in conjunction with weakly varying incidence angles. The f-theta optics therefore ensures that the focal region of the deflected laser beam moves on a plane and not on a spherical surface. The height adjustment of the lifting table is used to position the latter such that the focal plane coincides with the plane to be irradiated.

Since the apparatus 100 is set out for the purpose of processing relatively small substrates (for example with the maximum edge lengths in the range of 10 nm or less), the working area of the combination of galvanometer scanner 126 and imaging optics 128 can be relatively small, for example 20 mm×20 mm. It is therefore possible to focus the laser beams into a small focal region even with relatively cost-effective optics in the entire flat working area. In preferred embodiments, the spot size of the focused laser beam on the substrate, that is to say the diameter of the beam at the location of least diameter, can be, for example 20 µm or less, in particular 15 µm or less, or even 10 µm or less. As a rule, the diameter at the focus is greater than approximately 2 µm to 5 µm. At the same time, the depth of damage, which depends on the numerical aperture of the focused laser beam, can be kept relatively shallow, thus enabling an exact localization of the area to be weakened, both laterally and as regards depth. In preferred embodiments, the Rayleigh length characteristic of the depth of damage or of the depth of field of the beam can lie in the range of 100 µm or below, in particular in the range from 80 µm or thereunder or even 60 µm or thereunder. The Rayleigh length is defined here as a length measured along the beam direction which corresponds to the spacing between the location of minimum beam constriction (focal location) and that location where the beam diameter corresponds to twice the beam diameter at the focal location. A highly precise material damage that can also be delimited with local precision is therefore possible on the surface or in the interior of the substrate material.

The relatively small working area for the laser processing enables recourse to a relatively cost-effective lifting table for the movement system, and the relinquishing of complicated precision movement systems in the x- and y-directions, since it is possible for the focused laser beam to cover all locations within the working area with the aid of the galvanometer scanner and the telecentric f-theta optics even given a stationary substrate holder. A compact and cost-effective design of the overall apparatus is thereby promoted. Of course, it is also possible to equip the apparatus with a precision movement system which enables the sample table 102 to be moved transverse to the direction of incidence of the beam, that is to say in the x- and y-directions. In this case, a more cost-effective stationary optics can be used for beam focusing.

An observation system which comprises a surface camera 130 which can be aligned with the substrate surface is provided for supporting exact beam positioning on the substrate surface. A positioning system for exact positioning of the substrate with reference to the laser beam comprises a ranging sensor 140 for detecting the exact position of the substrate surface. In this embodiment, the laser ranging sensor 140 is used in conjunction with an automatic focusing process.

It is also possible to equip the laser microprocessing apparatus 100 with a marker detection system for detecting markers provided on the substrate, and to undertake automatically relative to the markers the definition of the target region in which the crossing region of the irradiation trajectories is to be located.

The sample preparation apparatus can be assigned a breaking device (not shown) with the aid of which the substrates pre-damaged with the aid of the laser beam can be broken along predefined surfaces in order to produce TEM samples.

All the components of the sample preparation apparatus 100 are connected to a central control and operating unit 160 which is formed in the case of the example by a control computer with user interface (screen, keyboard). The central control can be used, for example, to set or program specific operating parameters for the laser radiation source 120 and the beam deflecting system 126. For example, the output power and the repetition rate of the laser, as well as the scanning speed can be set. Moreover, before irradiation of the substrate begins an operator can use the control and operating unit with support from the observation system to stipulate precisely via appropriate input parameters the irradiation trajectories along which the substrate is to be irradiated, and where the crossing region is to lie between irradiation trajectories. This enables an exact target preparation including an exact stipulation of the wedge angle of the TEM sample. Furthermore, if required it is possible to set the local profile of the power density of the laser radiation acting on the substrate specifically so as, for example, to cause a region as undamaged as possible to remain in the immediate vicinity of the crossing region (compare, as well, explanations in conjunction with FIG. 4). To this end, it is then possible as the program runs to output appropriate control signals to the attenuator 123 and/or to the shutter 122, or the output power of the laser 120 can be changed directly in a variable fashion.

By suitable selection of the laser beam fluence, which is introduced either into the interior of the substrate to be separated or into the surface thereof, it is either possible to initiate the crack directly during the traversal of the trajectory, or a state of stress or a local thinning of material is produced, either of which can be used thereafter for crack initiation. If appropriate, it is possible to appeal to experience from the field of laser-assisted separation of materials for the purpose of optimizing the laser parameters. For example, it is known that bodies made from non-metallic inorganic material can be separated by local irradiation with laser radiation. In addition to methods which utilize a strongly localized temperature gradient for crack propagation (for example DE 693 04 194 T2 corresponding to EP 0 633 867 B1), there are also known for the purpose of separating micromechanical elements (MEMS) or semiconductor chips for example from WO 2003/077295 A1—methods in the case of which a semiconductor wafer to be separated is internally fused locally by a focused laser beam after application of a protective film, and a multiplicity of cracks are initiated at the weakened positions after the fitting of a stretchable film on the rear side. Finally, a method is also known, for example, from EP 1 338 371 A1, in which a finely focused laser beam of suitable wavelength is focused in the interior of a semiconductor wafer such that internal stresses are produced there which either lead directly to the breaking open of the material, or form the precondition for the separation. DE 10 2004 024 475 A1 discloses a method for separating semiconductor materials in the case of which a laser beam is directed onto a separation zone of the semiconductor material, the wavelength of the laser beam being selected in such a way that the laser beam is transmitted by the semiconductor material partially under partial absorption. To the extent that these documents include material-specific data for the design of laser parameters, these data can be used to optimize certain embodiments of the inventive method.

Given appropriate compensation by the processing software, a sample table inclined from horizontal by a few degrees (for example between 2° and 10°) can be used for the purpose of excluding feedback of the laser beam into the laser radiation source without having to use an expensive optical isolator. In the case of the example, the flat top side of the lifting table 102 is permanently slightly inclined such that the surface normal of the top side serving as holding surface is at a setting angle of approximately 5° to the direction of incidence of the laser beam 125 such that radiation reflected by the substrate surface cannot pass into the focusing optics 128.

In order to avoid undesired irradiation effects on the front side, resting on the substrate holder, of the substrate during the irradiation, the substrate holder (lifting table) consists, at least in the region of the substrate bearing surface, of a material which is transparent to the radiation of the laser such that no heat is developed during irradiation. Alternatively or in addition, it is possible to provide in the centre of the working area a, for example, top-shaped small cutout or opening such that the target area of the mounted substrate makes no physical contact with the substrate support.

After the input of all the control parameters required for the processing procedure, the sample preparation apparatus 100 executes the prescribed program automatically. The control parameters can be input separately before each process. It is also possible to store in a memory of the control and operating unit 160 various preprogrammed sets of control parameters which can be assigned to specific types of sample and can be retrieved "at the touch of a button".

Figure 2:
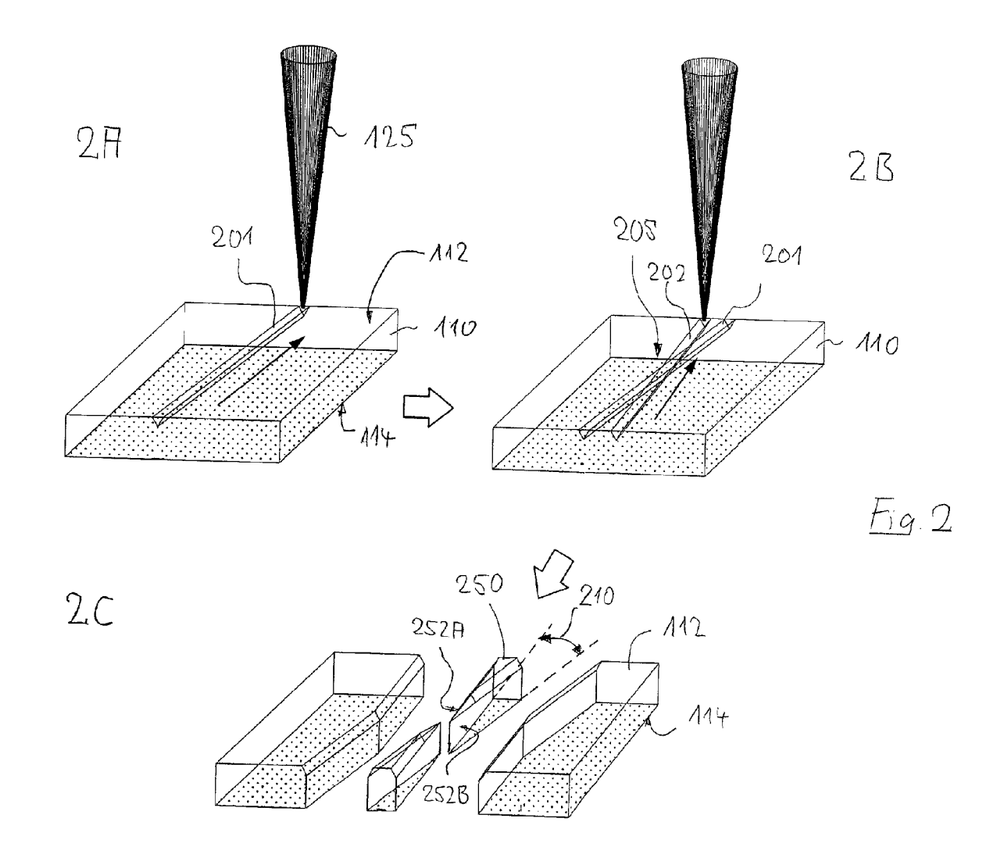
FIG. 2 shows a diagram of various method steps in the production of TEM samples by introduction of crossed weak paths on the surface of a substrate (laser scoring)

Various sample preparation methods which can be carried out semiautomatically or fully automatically with the aid of the sample preparation apparatus 100 are explained below with reference to FIGS. 2, 3 and 4. The starting point of the sample preparation explained with reference to FIG. 2 is a normally plane parallel thin section made from a monocrystalline, partially crystalline or polycrystalline or else amorphous sample material whose structure is to be examined within a near-surface inspection area (target area) which is of interest, as a cross-sectional preparation in the transmission electron microscope. The substrate can, for example, be a rectangular cutoff of a one-sidedly coated or uncoated semiconductor wafer. Typical sizes can lie in the range of 10 mm edge length or below.

That substrate surface whose vicinity the inspection area of interest lies forms the front side 114, illustrated by dots, of the substrate which, in many variants of the method, is not processed or modified mechanically or in another way during the sample preparation. Lying in the vicinity of the front side as a consequence of a structuring process in the case of the example are numerous layers which are made from different materials and have lying therebetween interface sections which run substantially parallel to the front side and are to be inspected.

When the substrate is not thin enough in the area of interest, the optimum thickness is attained by prior, plane parallel grinding of the rear side averted from the front side. As a rule, the optimum substrate thickness is a function of the substrate material and of the type of sample, but frequently lies in the range of between 30 µm and 500 to 550 µm.

Thereafter, the plane parallel substrate with the unprocessed front side 114 is laid onto a flat bearing surface, provided therefor, of the lifting table 102 and fastened on the lifting table with minimum stress, for example with the aid of a plurality of retaining springs acting on the substrate rear side 114 lying above. Thereafter, the lifting table is moved in a vertical direction such that the above lying rear side of the substrate lies substantially in the focusing plane of the laser beam or in the focal plane of the f-theta optics 128. As an alternative to retaining springs, fixing can also be performed with the aid of underpressure in the manner of a vacuum chuck. To this end, the holding table can consist, at least in the holding region, of porous ceramic material through which the substrate is sucked onto the bearing surface. It is also possible as a rule, to mount the substrate simply only on the bearing surface without fixing it separately.

In the case of the example, the substrate material is substantially impervious to the laser wavelength used or strongly absorbing, thus providing a rear-side, surface scoring with the aid of a focused laser beam (laser scoring).

After termination of the positioning, the first step is to introduce a first weak path 201 on the rear side 112 by traversing a first irradiation trajectory with the focused laser beam (FIG. 2A). In the case of the example, the first trajectory is rectilinear, but it can also be singly or multiply curved or kinked in other embodiments. Thereafter, a second irradiation trajectory is traversed, which can also be rectilinear, kinked or curved, the result being to produce in the case of the example a second, straight weak path 202 which is present, in turn, in the form of surface scoring.

The irradiation is controlled in this case in such a way that the first weak path crosses the second weak path, already running in the sample material, in a previously defined crossing region 205 of weak paths at an acute crossing angle 210 (typically less than 18.5°). In this case, the precise size of the crossing angle, and the precise shape of the two trajectories are a function of the respective substrate material and of the type of any coatings present.

As a rule, the radiation parameters of the focused laser beam are set as a function of the sample material and the nature of the surface of the substrate such that there is present in the region of the weak paths a depth of damage which is at least one third to two thirds of the substrate thickness, but can also go deeper, for example to 4/5 of the substrate thickness or more. However, it should not comprise the entire substrate thickness. The deeper the laser-induced material weakness goes, the higher is the probability that a locally defined crack will be produced in the substrate material in subsequent method steps. On the other hand, the processing depth should only be so deep that the structure of the sample material in the inspection area lying near the front side 114 remains as undamaged as possible and experiences no chemical or structural modification.

However, exceptions to this depth restriction can be favourable far removed from the target area at the start and, if appropriate, also at the end of an irradiation trajectory. At the start and at the end of an irradiation trajectory, the processing parameters can be set such that the substrate material is damaged over the entire depth and is, at it were, severed in this case. It is thereby possible to produce notches 410 (see FIG. 4) which promote the locally defined introduction of cracks during breaking.

After termination of the laser beam processing, in accordance with FIG. 2C the substrate is broken along the first weak path 201 and along the second weak path 202 by introducing a suitable mechanical stress into the substrate. In this case, starting from the weak paths specifically introduced locally fracture surfaces are produced whose course in the sample material is more or less prescribed by the orientation of the weak paths. It is thereby possible to produce one or two TEM samples 250 which respectively have a wedge-shaped sample section whose wedge surfaces 252A, 252B are formed by atomically smooth or faceted fracture surfaces. In the overwhelming number of experiments, these samples will have in the region of the wedge tip at least one electron-transparent region suitable for inspection by means of transmission electron microscopy.

A great advantage of the surface, rear-side laser scoring consists in that this method can be applied in the case of all sample materials, irrespective of whether the material is transparent, partially transparent or substantially absorbent for the laser radiation used. The processing of transparent materials in this case requires so-called multiphoton absorption, which can easily be stimulated by short pulse lasers and, occasionally, also by ultrashort pulse lasers.

Figures 3, 3A:
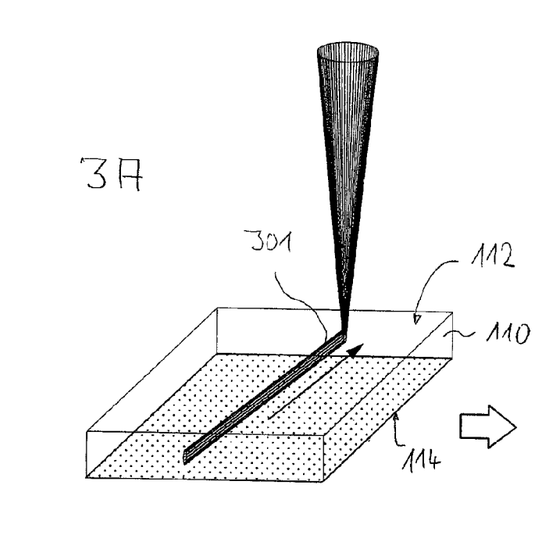
FIG. 3 shows a diagram of various method steps in the production of TEM samples by introducing crossed weak paths in the interior of a substrate.
Figures 3, 3B:
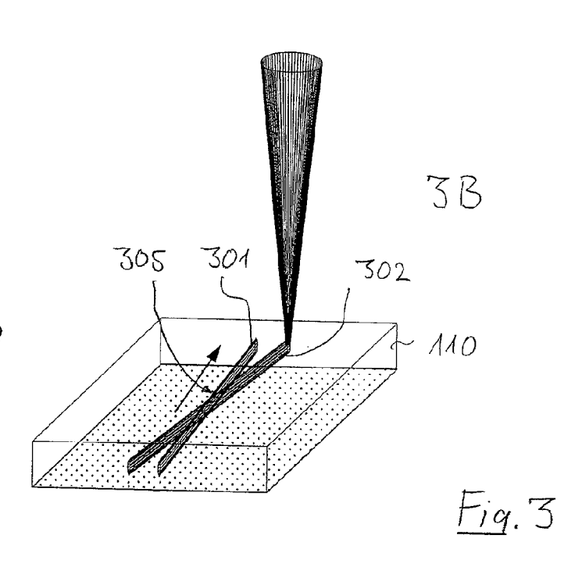
Figures 3, 3C:
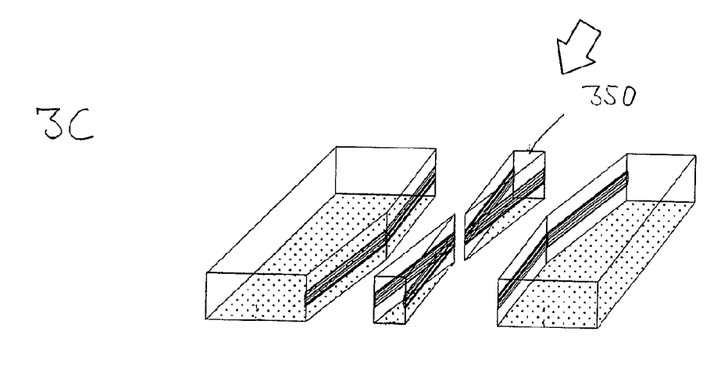
Figure 4:
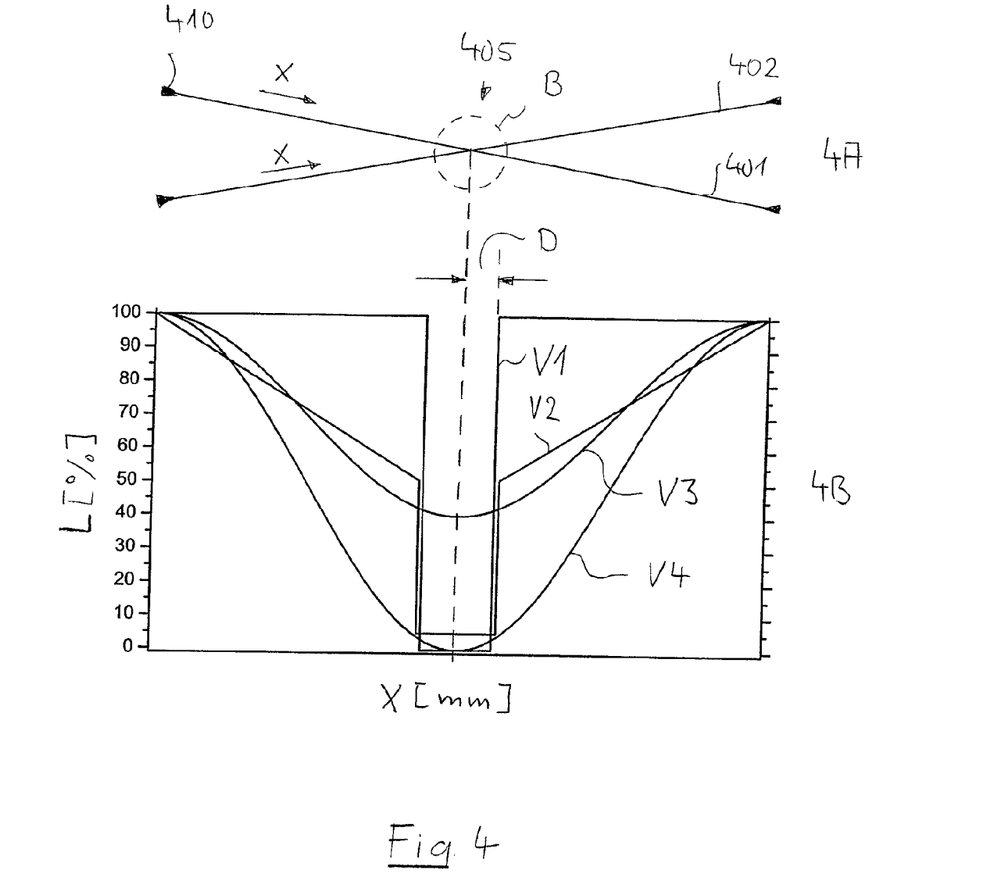
FIG. 4 shows a diagram of various possibilities for controlling the power of the laser radiation acting on the substrate such that a largely undamaged area remains in the immediate vicinity of the crossing region of irradiation trajectories.

The diagrammatic images in FIG. 3 explain method steps in the production of TEM samples from sample material which is at least partially transparent to the laser radiation wavelength used or relatively low in absorption. In such materials, the laser beam can be set such that the majority of the laser beam energy is concentrated in the interior of the sample material, that is to say between the substrate surface, thus resulting in internal processing of the substrate material or damage of the interior of the preparation. In the case of this method variant, the thin section serving as initial preparation is firstly polished from its rear side 112 so as to produce an optically smooth beam entrance surface with a mean surface roughness $R_a$ of less than approximately 10 nm. Substantially rougher surfaces can sometimes scatter the laser light coupled in too strongly, thus rendering the focusing of the laser beam energy in the interior of the sample more difficult and less accurate. (If the rear side of the substrate is already smooth enough, for example in the case of a semiconductor wafer polished on both sides, the polishing step can, of course, be omitted.) The subsequent method steps can be carried out similarly to the procedure in FIG. 2 by producing in the interior of the sample material firstly a first weak path 301 in accordance with FIG. 3A, and then a second weak path 302 in accordance with FIG. 3B which cuts the first weak path in a crossing region 305 and at an acute crossing angle. All the above-described methods for crack initiation and/or crack propagation can be used for subsequently breaking open the substrate to produce the wedge-shaped TEM sample 350.

Particularly in the case of heat-sensitive sample materials, method variants can be used in the case of which, during traversal of the irradiation trajectories, the laser irradiation can be controlled locally and/or temporally such that a substantially undamaged area remains in the immediate vicinity of the crossing region of the irradiation trajectories. The power density acting on the substrate can, for example, be reduced so far that the material-specific ablation threshold of the substrate material is undershot. Here, the ablation threshold is designated as that limiting power density or limiting fluence for which given a prescribed wavelength of the laser beam (also other properties of the laser beam such as, for example, duration and number of the pulses) the substrate material is removed. Same examples are explained with the aid of FIG. 4.

FIG. 4A shows the desired course of a first weak path 401 and of a second weak path 402 which pass over one another in a crossing region 405 at an acute angle of approximately 20°. In the case of heat-insensitive materials, during traversal of the corresponding irradiation trajectories the focused laser beam can have overall substantially the same power density as is explained with reference to examples in FIGS. 2 and 3. However, it is to be noted in this case that the target area lying in the vicinity of the wedge tips is exposed twice to the possibly damaging laser radiation, as a result of which the material to be inspected can possibly be modified such that the subsequent TEM inspection no longer shows the undamaged material which is actually of interest. In order to avoid thermal overheating of the crossing region, which can result from the altered geometric boundary conditions for heat transport, it is provided in the case of these method variants to exercise temporally and/or locally dependent control of the power P, acting in the focal region, of the laser beam such that the incident power density lies below a threshold power density leading to material modification in the hypothetical crossing region of the irradiation trajectories.

FIG. 4B shows a diagram of some local power density profiles. Plotted in this case on the abscissa is the location x along an irradiation trajectory, while the normalized power density, to which the substrate is exposed, is plotted on the ordinate. In accordance with the variant V1, the active power in the vicinity of the hypothetical crossing point of the irradiation trajectories is reduced to zero such that the irradiation range remains completely unirradiated, and the irradiation at a spacing D from the theoretical crossing point breaks off abruptly and is taken up again after running over the crossing point after a spacing D. The spacing D corresponds here, so to say, to the radius of the substantially unirradiated, or only weakly irradiated area B about the hypothetical crossing point. This power profile can be achieved, for example, by temporally dependent or locally dependent driving of the shutter 112 or, in the case of pulsed lasers, for example, by temporarily turning off the laser. In accordance with variant V2, the active power is reduced linearly at first as the focused laser beam approaches the crossing region, and is completely interrupted at the spacing D from the crossing region. This can be achieved by a combined driving of the attenuator 123 and the shutter 122, or by combined driving of the shutter in conjunction with a laser which can be controlled with regard to its output power.

When abrupt transitions are to be avoided between areas of laser irradiation and areas completely unirradiated, it is also possible to undertake a continuously variable, position-synchronous output of the laser power in the vicinity of the crossing region. In accordance with variant V3, in this case the power acting on the substrate is reduced only so far in the near region of the crossing point 405 that the active power lies below the material-specific damage threshold, although a certain degree of irradiation also occurs in the crossing region. In the case of variant V4, with the continuous change in the active laser power the latter is reduced as far as zero as the crossing point is approached, and then rises continuously again upon overshooting the crossing point. A continuously variable attenuator can be driven appropriately for these variants.

The spacing D between the hypothetical or actual crossing point 405 of the irradiation trajectories and the facing end of the damage path actually produced can be relatively small and, for example, lie between approximately 50 μm and approximately 300 μm, in order on the one hand to ensure that the crack propagation along an irradiation trajectory also advances through the crossing region, not irradiated as far as being damaged, up to the respectively opposite end of the damaged zone, and in order, on the other hand, to ensure the irradiation power density is reduced in the immediate vicinity of the crossing point so as to save the material. Corresponding values for the spacing D and the locally dependent power profile are best established experimentally with the aid of a few samples, and can then be programmed for samples of similar type before the production of samples, or be stored in a fixed data record for specific types of sample.

Figure 5:
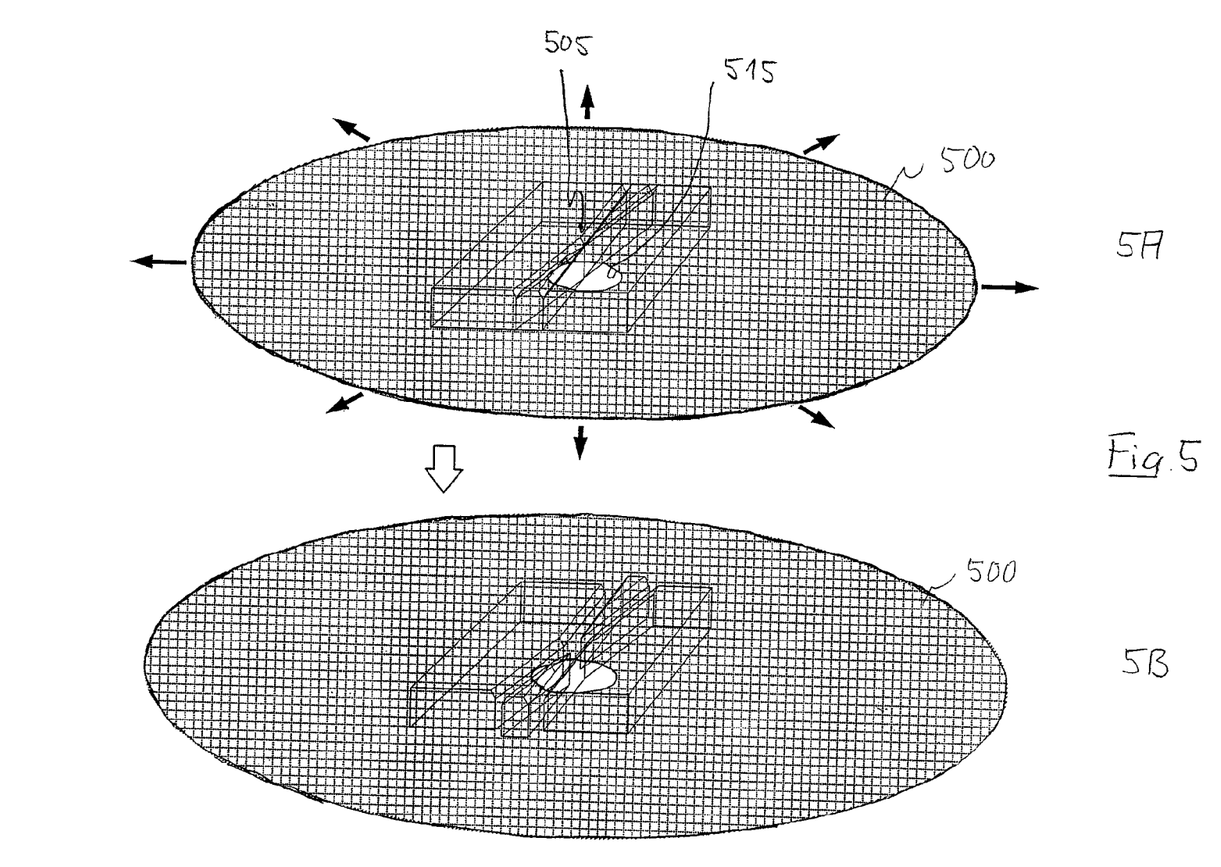
FIG. 5 shows a diagram of the separation of a substrate along the weak paths with the aid of a stretchable adhesive film.

For the crack initiation following termination of the laser processing, the sample to be processed can, for example, be bonded onto a so-called dicing tape with its front side or rear side, that is to say onto a film which adheres very well to the surface and enables crack initiation by stretching. In the case of the preferred mode of procedure explained in more detail with reference to FIG. 5, use is made of a stretchable film 500 which has a circular opening 515 in the vicinity of the crossing region 505 of the two damage paths, such that the extremely sensitive, acutely angled, wedge-shaped ends of the triangles enclosed by the laser trajectories are exposed. The diameter of the cutout can lie, for example, in the range of 1 mm or less. As shown in FIG. 5A, the isotropically expandable film 500 is bonded onto the front side, opposite the scored rear side of the substrate (illustrated as transparent), of the substrate in such a way that the mutually facing tips of the wedges project freely into the region of the cutout 515 free from an adhesive layer. Subsequently, the expandable adhesive film is stretched in all directions such that the parts of the predamaged sample which adhere thereto are put under tensile stress substantially in a radial direction. In this case, starting from the damage paths cracks propagate in the sample material which finally lead to the production of the wedge-shaped sample sections which still adhere to the adhesive film with their broader ends.

Figure 6:
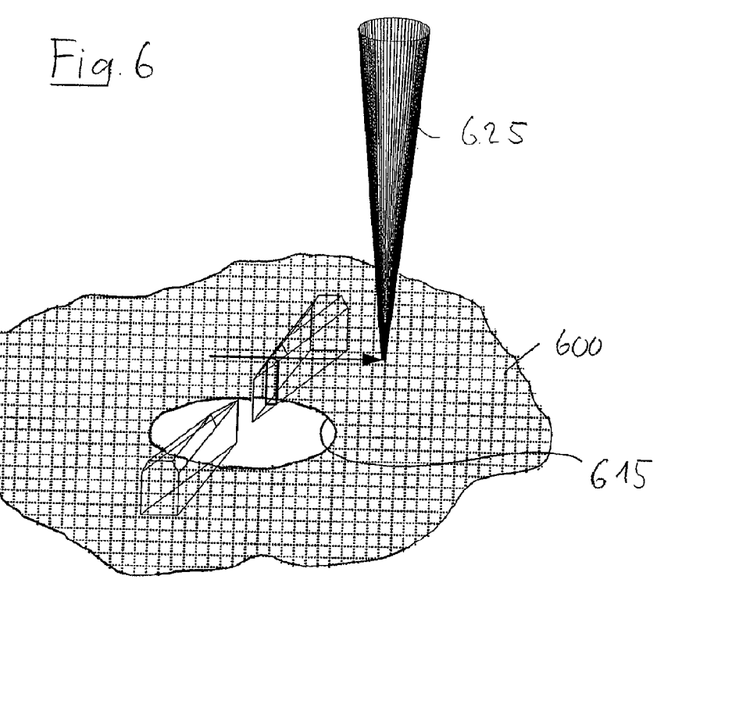
FIG. 6 shows a diagram of how a focused laser beam is used to separate off a sample section provided for the TEM inspection.

The wedge-shaped sample sections can then be detached as a whole from the adhesive film. In the case of a method variant illustrated diagrammatically in FIG. 6, a section can remain on the film which makes contact adhesively with the film, while the wedge-shaped tip region projecting freely into the region of the cutout is separated with the aid of a focused laser beam 625. In the case of this variant, it is possible to dispense with using heat and/or chemicals which frequently have to be used in other instances in order to separate from the film the sample piece adhering to the film. Consequently, after the stretching the two wedges can be separated off by laser cuts without impairing the electron-transparent areas.

Alternatively, however, it is also possible to apply other methods for crack initiation such as, for example, breaking over an edge. The substrate provided in a defined fashion with linear weak paths can also be broken by mounting it on a support of limiting flexibility and subsequently breaking it by applying forces. The support can be formed, for example, by a gel substance which is sucked firmly against the smooth substrate surface and can be removed again from the sample without residue after the breaking of the sample by carefully and slowly putting the sample on an edge. In this case, the crossing region can be positioned over an opening of the flexible material so that the crack-promoting forces are introduced only from the sides, but not directly at the crossing region. The sensitive areas at the wedge tips are thereby spared.

In general, it is also possible to damage the substrate initially only along one path, then to break it along this path, and subsequently to provide the second damage path. To the extent that the sample material naturally has cleavage planes, the substrate can also initially be broken along a natural cleavage plane before a damage path of suitable alignment is then brought up at an acute angle to the already existing fracture edge. It is also possible firstly to score with the aid of a laser beam and break along the laser-induced weak path, and after that to produce the break along the natural cleavage plane.

Figure 7:
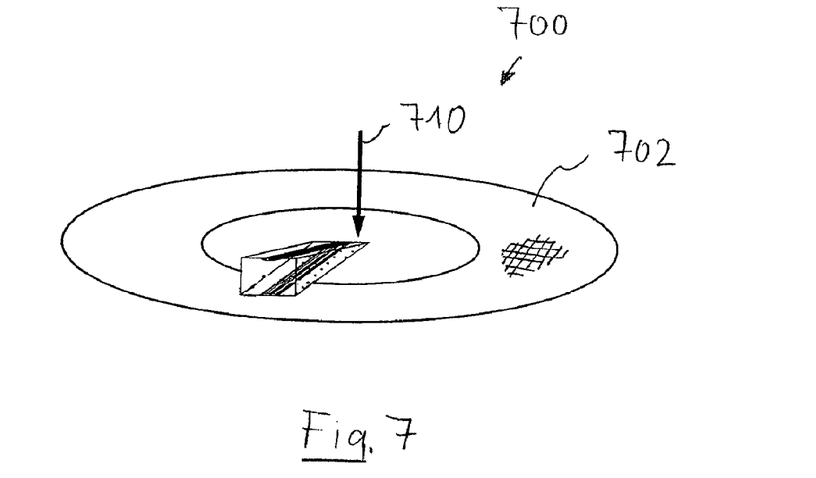
FIG. 7 shows a diagram of a sample holder provided for installation in a transmission electron microscope, together with a wedge-shaped preparation fastened thereon.

Wedge-shaped preparations produced in accordance with the invention are electron-transparent in the region of the wedge tip and can be inspected by means of a transmission electron microscope after being suitably mounted on a carrier. One possibility of this is explained in more detail in conjunction with FIG. 7.

As a rule, the substantially wedge-shaped preparations produced are not directly suitable for fitting in a sample holder of a transmission electron microscope. Consequently, it is advantageous as a rule to fasten the wedge-shaped preparation produced on or in a TEM sample carrier whose external dimensions are adapted to the geometry of the sample holder in the transmission microscope. The TEM sample carrier 700 in FIG. 7 consists essentially of a flat ring 702 whose outside diameter is adapted to the inside diameter of a TEM sample holder in the transmission electron microscope, and which has in its interior a through hole 704 through which the electron beam is guided during the TEM inspection. The ring 702 can have a reticular structure which consists essentially of electrically conductive material, for example a metal such as copper. The carrier net can be fabricated, for example, with the aid of a laser microprocessing system. The wedge-shaped TEM sample is now fastened on the top side of the ring 702 with its thicker end by bonding or in another way for the purpose of inspection such that the electron-transparent region in the vicinity of the wedge tip is arranged approximately in the centre of the ring in such a way that it can be transilluminated by an electron beam 710. The latter transirradiates the interface regions between the layers of the near-surface structure in a fashion substantially perpendicular to the normal direction of the layers so as to enable a high resolution interface analysis.

The wedge-shaped TEM sample can be fitted manually on the TEM sample carrier after being produced. In one embodiment of a sample preparation apparatus, however, this fitting can be automated. To this end, the sample preparation apparatus is assigned a microrobotic system for automatically transferring the wedge-shaped TEM samples onto a TEM sample carrier.

The above description of the preferred embodiments has been given by way of example. From the disclosure given, those skilled in the art will not only understand the present invention and its attendant advantages, but will also find apparent various changes and modifications to the structures and methods disclosed. It is sought, therefore, to cover all changes and modifications as fall within the spirit and scope of the invention, as defined by the appended claims, and equivalents thereof.

What is claimed is:

1. A method for producing samples for transmission electron microscopy, comprising:
   preparing from a substrate of a sample material a sample which has a wedge-shaped sample section which is bounded by wedge surfaces and has in the region of a wedge tip at least one electron-transparent region, the preparing step comprising:
   irradiating the sample material by means of a laser beam along a first irradiation trajectory in order to produce a first weak path in the sample material, the irradiation being controlled such that the first weak path crosses a second weak path, running in the sample material, at an acute angle in a crossing region; and
   breaking the substrate along the first weak path and along the second weak path.

2. The method according to claim 1, wherein the sample material is irradiated along a second irradiation trajectory by means of a laser beam in order to produce the second weak path, such that the first weak path and the second weak path running at an acute angle to one another are produced by irradiation of the sample material by means of a laser beam.

3. Method according to claim 1, wherein the first and the second weak paths are orientated relative to one another such that the acute angle present between the first and second weaks path in the crossing region is 25° or less.

4. The method according to claim 1, wherein an inspection area provided for inspection by means of transmission electron microscopy lies near a front side of the substrate, and the irradiation is performed by means of the laser beam from the rear side, opposite the front side, of the substrate.

5. The method according to claim 4, wherein the irradiation is controlled such that the inspection area lying near the front side lies outside the weak path.

6. The method according to claim 4, wherein before the irradiation the substrate is polished on its rear side in order to produce a relatively smooth radiation entrance surface having a mean depth of roughness $R_a$ of less than 10 nm.

7. The method according to claim 1, wherein before the irradiation the substrate has a substrate thickness between 30 μm and 550 μm in the area provided for irradiation.

8. The method according to claim 1, wherein the irradiation is carried out by means of laser radiation to which the sample material is at least partially transparent, and the irradiation is controlled so as to produce an inner weak path lying in the interior of the substrate at a spacing from the substrate surface.

9. The method according to claim 1, wherein the irradiation is carried out by means of laser radiation for which the sample material is strongly absorbing.

10. The method according to claim 1, wherein the irradiation is controlled so as to produce a weak path near the surface on the irradiation side of the substrate.

11. The method according to claim 1, wherein the laser radiation produces a depth of damage which corresponds at least to a third of the thickness of the substrate in the region of the weak path.

12. The method according to claim 1, wherein in the inspection area the sample material has a layer structure with one or more layers and one or more interfaces, the weak paths being orientated so as to produce wedge surfaces which are substantially perpendicular to at least one of the interfaces.

13. The method according to claim 1, wherein a tunable laser source produces the laser radiation.

14. The method according to claim 1, wherein the irradiation is carried out by means of an ultrashort pulse laser with characteristic pulse durations in the region of picoseconds or femtoseconds.

15. The method according to claim 1, wherein the laser radiation is irradiated into the substrate obliquely in relation to a surface normal of a radiation entrance surface.

16. The method according to claim 1, wherein during traversal of an irradiation trajectory control is exercised locally in order to vary the power density acting on the substrate.

17. The method according to claim 16, wherein the irradiation is controlled such that a substantially undamaged area remains in an immediate vicinity of the crossing region.

18. The method according to claim 17, wherein a radius of the substantially undamaged area is less than 300 µm.

19. The method according to claim 17, wherein at least one of the following steps is performed during traversal of an irradiation trajectory, in order to produce the substantially undamaged area:
   (i) the laser beam is briefly interrupted by means of a controllable beam interruption device when the crossing region is passed over,
   (ii) the laser is briefly turned off when the crossing region is passed over;
   (iii) an active output power of the laser is controlled locally, the power density acting on the substrate being reduced when the crossing region is passed over.

20. The method according to claim 16, wherein, during traversal of an irradiation trajectory, a power density acting on the substrate is controlled locally so as to entirely sever the substrate far from the crossing region of the irradiation trajectories at least one of a start and an end of an irradiation trajectory such that a notch results.

21. The method according to claim 1, wherein the production of the first weak path and the production of the second weak path are carried out automatically with the aid of a programmable laser microprocessing apparatus.

22. The method according to claim 1, wherein in order to break the substrate, a stretchable film is bonded onto a side of the substrate, and a force sufficient for at least one of crack initiation and crack propagation is subsequently exerted on the substrate by stretching the film.

23. The method according to claim 22, wherein the film has a region lacking an adhesive layer and is bonded onto the substrate in such a way that the region lacking an adhesive layer lies in the region of the crossing of the weak paths.

24. Sample for transmission electron microscopy, comprising:
   a wedge-shaped sample section which is bounded by fracture surfaces and has in the region of a wedge tip at least one electron-transparent region,
   the sample being prepared by the method according to claim 1.

25. An apparatus for producing samples for transmission electron microscopy, comprising:
   a substrate holder for holding a substrate made from a sample material;
   a laser system having a laser radiation source and a beam guiding system for guiding a laser beam onto a beam entrance surface of the substrate;
   a movement system for producing a relative movement between the substrate and the laser beam in such a way that the substrate is irradiated by the laser beam along a first irradiation trajectory so as to produce a first weak path in the sample material; and
   a control device which is configured in such a way that the irradiation is controlled such that the first weak path crosses a second weak path, running in the sample material, at an acute angle in a crossing region.

26. The apparatus according to claim 25, wherein the control device is configured in such a way that the sample material is irradiated by means of the laser beam along a second irradiation trajectory so as to produce the second weak path, which second weak path crosses the first weak path at an acute angle in a crossing region, wherein the apparatus is configured to carry out the production of the first weak path and the production of the second weak path automatically on the basis of control signals from the control device.

27. The apparatus according to claim 25, wherein the control device in configured to be programmed by inputting a plurality of input parameters, the input parameters comprising at least the following input parameters:
   a target area parameter which represents the position of the target area in which a first irradiation trajectory crosses a second weak path at an acute crossing angle; and
   a crossing angle parameter which represents directly or indirectly the crossing angle of the first weak path with the second weak path.

28. The apparatus according to claim 27, wherein the input parameters further include at least one of the following input parameters:
   a profile parameter which represents a local profile at least of one irradiation trajectory;
   a focusing parameter which defines the position of the focal region on the substrate or in the substrate;
   at least one laser parameter which defines the beam characteristics of the laser beam focused onto the substrate; and
   a power variation parameter which represents parameters for the position-synchronous variable control of the laser power density acting on the substrate.

29. The apparatus according to claim 25, wherein the control device is configured to be programmed to exercise control locally in order to vary the power density acting on the substrate during traversal of an irradiation trajectory.

30. The apparatus according to claim 25, wherein the control device is configured in such a way that the irradiation is controlled such that a substantially undamaged area remains in the immediate vicinity of the crossing region.

31. The apparatus according to claim 30, wherein a radius of the substantially undamaged area is less than 300 µm.

32. The apparatus according to claim 30, wherein the apparatus is configured in such a way that in order to produce the substantially undamaged area, at least on of the following is provided:
   (i) the laser system has a controllable beam interruption device, and the control device is configured in such a way that during traversal of an irradiation trajectory, in order to produce the substantially undamaged area the laser beam is briefly interrupted by means of the controllable beam interruption device when the crossing region is passed over;
   (ii) the laser radiation source can be turned off briefly, and the control device is configured in such a way that during traversal of an irradiation trajectory, in order to produce the substantially undamaged area the laser radiation source is briefly turned off when the crossing region is passed over;
   (iii) the control device is configured in such a way that in order to produce the substantially undamaged area, the active output power of the laser radiation source is controlled locally, the power density acting on the substrate being reduced when the crossing region is passed over.

33. The apparatus according to claim 25, wherein the substrate holder has a lifting table capable of being moved exclusively in the direction of a mean direction of incidence of the laser beam.

34. The apparatus according to claim 25, wherein the substrate holder is assigned a tilting arrangement for producing a temporary or permanent inclination of a surface normal of a substrate holding surface in relation to the direction of incidence of the laser beam.

35. The apparatus according claim 25, wherein the substrate holder comprises at least one of the following features:
   (i) the substrate holder consists of a material transparent to the radiation of the laser, at least in the region of the substrate bearing surface,
   (ii) an opening is provided in the centre of the work area in the substrate holder such that it is possible to mount a substrate in such a way that the target area of the mounted substrate makes no physical contact with the substrate holder.

36. The apparatus according to claim 25, wherein the laser radiation source comprises at least one of:
   (i) an ultrashort pulse laser,
   (ii) a fibre laser; and
   (iii) a tunable laser.

* * * * *